United States Patent
Ogawa

(10) Patent No.: US 6,707,059 B1
(45) Date of Patent: Mar. 16, 2004

(54) SOLID STATE RADIATION DETECTOR

(75) Inventor: Masaharu Ogawa, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/620,707

(22) Filed: Jul. 20, 2000

(30) Foreign Application Priority Data

Jul. 22, 1999 (JP) ............................................. 11-207283

(51) Int. Cl.[7] .............................................. G01N 23/04
(52) U.S. Cl. ....................................... 250/591; 250/580
(58) Field of Search ................................ 250/591, 580, 250/370.07, 370.08, 370.09; 257/431; 378/28, 31; 430/56, 57.1, 57.2, 58.05, 58.1

(56) References Cited

U.S. PATENT DOCUMENTS

| | | | | |
|---|---|---|---|---|
| 5,508,507 A | * | 4/1996 | Nelson et al. | 250/591 |
| 6,218,668 B1 | * | 4/2001 | Luke | 250/370.01 |
| 6,376,857 B1 | | 4/2002 | Imai | |
| 6,455,867 B2 | * | 9/2002 | Ogawa | 250/580 |

FOREIGN PATENT DOCUMENTS

| | | | | |
|---|---|---|---|---|
| EP | 898421 A2 | * | 2/1999 | H04N/5/30 |
| EP | 0898421 A2 | * | 2/1999 | H04N/5/30 |
| EP | 1 041 400 A2 | | 4/2000 | |
| EP | 1 041 401 A2 | | 4/2000 | |
| JP | 10-271374 | | 10/1998 | H04N/5/225 |
| JP | 11-87922 | | 3/1999 | H05K/3/46 |
| JP | 11-89553 | | 4/1999 | C12M/1/00 |

OTHER PUBLICATIONS

Abstract 10–271374 Oct. 9, 1998.
Abstract 11–087922 Mar. 30, 1999.
Abstract 11–089553 Apr. 6, 1999.

* cited by examiner

*Primary Examiner*—Edward J. Glick
*Assistant Examiner*—Chin-Cheng Glen Kao
(74) *Attorney, Agent, or Firm*—Sughrue Mion, PLLC

(57) ABSTRACT

A solid state radiation detector 20 is formed by stacking a first electrode layer 21, a recording photoconductive layer 22, a charge transfer layer 23, a reading photoconductive layer 24, and a second electrode layer 26 having a stripe electrode 26 consisting of main elements 26a, in the recited order. A large number of secondary elements 27a, for outputting an electrical signal which has a level proportional to a quantity of latent image charge stored in a charge storage portion 29 formed in the interface between the recording photoconductive layer 22 and the charge transfer layer 23, are provided so that the main and secondary elements are alternately arranged in parallel to one another. The width $W_b$ of the main element 26a, the transmission factor $P_b$ of the main element 26a with respect to the reading light, the width $W_c$ of the secondary element 27a, and the transmission factor $P_c$ of the secondary element 27a with respect to the reading light are determined so that they satisfy a condition equation of $(W_b \times P_b)/(W_c \times P_c) \geq 1$.

10 Claims, 6 Drawing Sheets

XZ-SECTION

XY-SECTION

XZ-SECTION

XY-SECTION

XZ-SECTION

XY-SECTION

XZ - SECTION

XY - SECTION $(Wb \times Pb)/(Wc \times Pc) \gtrsim 1$ ··· CONDITION EQ. (1)
$(Wb \times Pb)/(Wc \times Pc) \gtrsim 5$ ··· CONDITION EQ. (2)
ELECTRODE CONSTRUCTION (CORRESPONDING TO 2 CYCLES)

| | (1)/(2) | 26a | 27a | 26a | 27a | ENHANCEMENT IN EFFICIENCY |
|---|---|---|---|---|---|---|
| (a) | ○/○ | Pb=0.5, Wb=1 | Pc=0.05, Wc=1 | Pb=0.5, Wb=1 | Pc=0.05, Wc=1 | ◎ |
| (b) | ○/× | Pb=0.5, Wb=1 | Pc=0.25, Wc=1 | Pb=0.5, Wb=1 | Pc=0.25, Wc=1 | ○ |
| (c) | ○/× | Pb=0.5, Wb=0.5 | Pc=0.2, Wc=1 | Pb=0.5, Wb=0.5 | Pc=0.2, Wc=1 | ○ |
| (d) | ○/× | Pb=0.5, Wb=0.25 | Pc=0.1, Wc=1 | Pb=0.5, Wb=0.25 | Pc=0.1, Wc=1 | ○ |
| (e) | ×/× | Pb=0.5, Wb=0.25 | Pc=0.25, Wc=1 | Pb=0.5, Wb=0.25 | Pc=0.25, Wc=1 | × |
| (f) | ×/× | Pb=0.5, Wb=0.5 | Pc=0.3, Wc=1 | Pb=0.5, Wb=0.5 | Pc=0.3, Wc=1 | × |

○: THE CONDITION EQUATION IS SATISFIED
×: THE CONDITION EQUATION IS NOT SATISFIED

◎: EXTREMELY SATISFACTORY
○: SATISFACTORY
×: UNSATISFACTORY

FIG. 5

SOLID STATE RADIATION DETECTOR

BACKGROUND OF THE INVENTION

1. Field of the Invention

The present invention relates to a solid state radiation detector with a storage portion for storing a quantity of electric charge proportional to a quantity of radiation irradiated or quantity of light emitted by excitation of the radiation, as latent image charge.

2. Description of the Related Art

Today, in the field of radiation photography with the object of medical analysis, etc., a wide variety of radiation image information recording-reading units have been proposed and put to practical use. The recording-reading unit uses a solid state radiation detector or static storage medium (also stated as simply a detector), which temporarily stores electric charge obtained by detecting radiation, as latent image charge in its charge storage portion and also converts the stored latent image charge to an electrical signal representing radiation image information and outputs the converted signal.

Various types have been proposed as solid state radiation detectors that are used in the recording-reading unit. For instance, there is an optical reading type which employs the process of reading out a stored electric charge from the detector. In this type of detector, the stored electric charge is read out by irradiating reading light (e.g., electromagnetic waves for reading) to the detector.

The applicant of this application has proposed, in Japanese Patent Application Nos. 10 (1998)-271374, 11 (1999)-87922, and 11 (1999)-89553 published as Japanese Unexamined Patent Publication Nos. 2000-162726. 2000-284056, and 2000-284057, respectively, a solid state radiation detector of an optical reading type in which high-speed reading responsivity is compatible with efficient fetching of signal charge from the detector. The detector is constructed of (1) a first electrode layer (conductive layer) which has permeability with respect to recording radiation, or light emitted by excitation of the radiation (hereinafter referred to as recording radiation, etc.), (2) a recording photoconductive layer which exhibits electric conduction when irradiated with the recording light, etc., (3) a charge transfer layer which operates as substantially an insulator with respect to an electric charge of the same polarity as electric charge on the first electrode layer and also operates as substantially an electric conductor with respect to an electric charge of the opposite polarity, (4) a reading photoconductive layer which exhibits electric conduction when irradiated with reading light (electromagnetic waves for reading), and (5) a second electrode layer (conductive layer) which has permeability with respect to the reading light, which are stacked in the recited order. In this type of detector, signal charge (latent image charge) carrying image information is stored in a charge storage portion formed in the interface between the recording photoconductive layer and the charge transfer layer.

Particularly, in the above-mentioned Japanese Patent Application Nos. 11 (1999)-87922 and 11 (1999)-89553, there is proposed a detector where the electrode (light irradiating electrode) of a second conductive layer having permeability with respect to reading light is constructed with a stripe electrode consisting of a large number of main line electrodes. Also, a great number of secondary line electrodes, for outputting an electric signal which has a level proportional to a quantity of latent image charge stored in the charge storage portion, are provided within the second conductive layer so that the main and secondary line electrodes are alternately arranged in parallel to one another.

Thus, by providing the charge fetching electrode which consists of secondary line electrodes, within the second electrode layer, an additional capacitor is formed between the charge storage portion and the secondary line electrodes, and a transfer charge of the opposite polarity from the latent image charge stored in the charge storage portion by recording can be transferred to the secondary line electrodes by charge rearrangement at the time of reading. This can make smaller the quantity of the aforementioned transfer charge distributed to the capacitor formed between the main line electrodes and the charge storage portion through the reading photoconductive layer, compared with the case where the secondary line electrodes are not provided. As a result, the quantity of signal charge that can be fetched from the detector is made larger and therefore the fetch efficiency is enhanced. In addition, high-speed reading responsivity is compatible with efficient fetching of signal charge.

However, in the case where the-transmission factor of each main line electrode of the stripe electrode with respect to the reading light is small, or the case where the transmission factor of each secondary line electrode of the charge fetching electrode with respect to the reading light is great, even if the secondary line electrodes are provided within the second electrode layer, there is a possibility that a quantity of signal charge that can be fetched from the detector will become smaller. In addition, the quantity of signal charge that can be fetched from the detector varies depending on the area of the main or secondary line electrodes.

SUMMARY OF THE INVENTION

The present invention has been made in view of the aforementioned drawbacks found in the prior art. Accordingly, it is the primary object of the present invention to provide a solid state radiation detector which is capable of reliably making larger a quantity of signal charge that can be fetched therefrom.

The inventors of this application, in the detectors disclosed in the aforementioned [publication] Japanese Patent Application No. 11 (1999)-87922, particularly the detector where the main line electrodes and the secondary line electrodes are provided in the secondary electrode layer so that the main and secondary line electrodes are alternately arranged in parallel to one another, have made various investigations and experiments with respect to the relationship between the transmission factors and areas of the main and secondary line electrodes with respect to reading light and the magnitude of a quantity of signal charge that can be fetched from the detector, and have found the following relationship therebetween.

(1) The quantity of signal charge that can be fetched from the detector becomes larger, if the total quantity (quantity of light transmitted) R1 of the reading light incident on the reading photoconductive layer through the main line electrodes forming the stripe electrode for light irradiation is larger and also the total quantity R2 of the reading light incident on the reading photoconductive layer through the secondary line electrodes is smaller, that is, if the ratio R1/R2 of the total light quantity R1 of the former to the total light quantity R2 of the latter is greater.

Note that in the case where the distance between the main line electrode, for light irradiation and the secondary line electrode is not negligible with respect to the electrode width, there is a need to take this distance between electrodes into consideration. However, the space between electrodes is normally set small and filled with a material which intercepts the reading light. Therefore, the influence of the space on the quantity of signal charge is considered practically negligible.

(2) The total quantity of the reading light incident on the reading photoconductive layer through the electrodes is proportional to the product of the areas of the electrodes and the transmission factor with respect to the reading light, if the irradiation intensity of the reading light is the same. Since the length of the main line electrode for light irradiation is essentially the same as that of the secondary line electrode, the total quantity of the reading light incident on the reading photoconductive layer through the electrodes is considered practically proportional to the product of the widths of the electrodes and the transmission factor. That is, it is considered that R1 equals $W_b \times P_b$ and R2 equals $W_c \times P_c$.

(3) Therefore, both the transmission factor of each electrode with respect to the reading light and the electrode width need to be considered in order to reliably make larger a quantity of signal charge that can be fetched from the detector. If at least the ratio R1/R2 of the total light quantities is 1 or greater, it is considered that a sufficient quantity of signal charge can be obtained even when the transmission factor of the main line electrode with respect to the reading light is, for example, about 50%.

The present invention has been made based on the aforementioned new knowledge. That is, a solid state radiation detector according to the present invention comprises a first electrode layer having permeability with respect to recording radiation, or light emitted by excitation of the radiation; a recording photoconductive layer which exhibits electric conduction when irradiated with the recording radiation or the light; a reading photoconductive layer which exhibits electric conduction when irradiated with reading light; and a second electrode layer constructed of a large number of main line electrodes having permeability with respect to the reading light. The first electrode layer, the recording photoconductive layer, the reading photoconductive layer, and the second electrode layer are stacked in the recited order. A large number of secondary line electrodes, for outputting an electrical signal which has a level proportional to a quantity of latent image charge stored in a charge storage portion formed between the recording photoconductive layer and the reading photoconductive layer, are provided within the second electrode layer so that the main and secondary line electrodes are alternately arranged in parallel to one another. The width $W_b$ of the main line electrode, the transmission factor $P_b$ of the main line electrode with respect to the reading light, the width $W_c$ of the secondary line electrode, and the transmission factor $P_c$ of the secondary line electrode with respect to the reading light satisfy the following condition equation (1):

$$(W_b \times P_b)/(W_c \times P_c) \geq 1 \qquad (1)$$

The above-mentioned condition equation (1) means that the total quantity (quantity of light transmitted) of the reading light incident on the reading photoconductive layer through the main line electrodes is always larger than the total quantity (quantity of light transmitted) of the reading light incident on the reading photoconductive layer through the secondary line electrodes, in spite of the electrode widths and transmission factors of the main and secondary line electrodes, and also in spite of the quantity of the reading light.

Note that it is desirable that the right side of the equation be 5, and more desirable that it be 8. Furthermore, it is desirable that the right side of the equation be 12.

In the case where a plurality of main and secondary line electrodes are allocated to 1 pixel, preferably the ratio of the product of the width and transmission factor of the main line electrode per pixel and the product of the width and transmission factor of the secondary line electrode per pixel is determined so that it satisfies the above-mentioned condition equation. For instance, in the case where the transmission factors of the main line electrodes are all the same and also the transmission factors of the secondary line electrodes are all the same, the sum total ($W_b$) of the widths of the main line electrodes and the sum total ($W_c$) of the widths of the secondary line electrodes are set so that they satisfy the above-mentioned condition equation. Also, in the case where the transmission factors of the main line electrodes differ from one another, the case where the transmission factors of the secondary line electrodes differ from one another, and furthermore, the case where the number of main line electrodes differs from that of secondary line electrodes, the product of the width and transmission factor of each main line electrode in 1 pixel and the product of the width and transmission factor of each secondary line electrode in 1 pixel are calculated and then the ratio of the total sums is set so that it satisfies the above-mentioned equation (1). This can be represented by the following condition equation (2):

$$\frac{WP_b}{WP_c} = \frac{\sum_{i=1}^{m} W_{bi} \times W_{bi}}{\sum_{j=1}^{n} W_{cj} \times P_{cj}} \geq 1 \qquad (2)$$

in which $WP_b$ is the product of the width and transmission factor of the main line electrode per pixel, $WP_c$ is the product of the width and transmission factor of the secondary line electrode per pixel, m is the number of main line electrodes per pixel, $W_{bi}$ is the width of each main line electrode, $P_{bi}$ is the transmission factor of each main line electrode, n is the number of secondary line electrodes per pixel, $W_{cj}$ is the width of each secondary line electrode, and $P_{cj}$ is the transmission factor of each secondary line electrode.

As with the aforementioned condition (1), it is desirable that the right side of the equation be 5, and more desirable that it be 8. Furthermore, it is desirable that the right side of the equation be 12.

To satisfy the above-mentioned condition (1) or (2), it is preferable that the material of the main line electrode for light irradiation be any one among indium tin oxide (ITO), Idemitsu indium X-metal oxide (IDIXO, produced by Idemitsu Kosan), aluminum, and molybdenum, and it is preferable that the material of the secondary line electrode be any one among aluminum, molybdenum, and chrome.

The expression "charge storage portion formed between the recording photoconductive layer and the reading photoconductive layer" as used herein and in the appended claims is intended to mean a charge storage portion for storing a quantity of electric charge, generated within the recording photoconductive layer when irradiated with radiation carrying image information or irradiated with light emitted by excitation of the radiation, which is proportional to the quantity of the radiation or quantity of the light emitted by excitation of the radiation.

The method of forming the charge storage portion may employ, for example, a method of forming a charge storage portion in the interface between a charge transfer layer and a recording photoconductive layer (see the aforementioned Japanese Patent Application Nos. 10 (1998)-27137 and 11

(1999)-87922, filed by the applicant of this application), a method of forming a charge storage portion within a trapping layer or in the interface between the trapping layer and a recording photoconductive layer (see U.S. Pat. No. 4,535,468), or a method of providing micro conductive members on which latent image charge is concentrated (see the aforementioned Japanese Patent Application No. 11 (1999)-89553, filed by the applicant of this application).

Note that when recording or reading out a radiation image by the use of the detector of the present invention, a conventional recording and reading method and a unit thereof can be utilized as they are, without changing them.

The present invention has been made based on the new knowledge on the relationship between the transmission factors and areas of the main and secondary line electrodes with respect to the reading light and the quantity of signal charge that can be fetched from the detector, and in consideration of both the transmission factor of each electrode with respect to the reading light and the width of the main line electrode in order to reliably make larger a quantity of signal charge that can be fetched from the detector, the width $W_b$ of the mainline electrode, the transmission factor $P_b$ of the main line electrode with respect to the reading light, the width $W_c$ of the secondary line electrode, and the transmission factor $P_c$ of the secondary line electrode with respect to the reading light are set so that they satisfy the aforementioned condition equation (1). Therefore, regardless of the sizes of $W_c$ and $W_b$, the detector of the present invention is capable of reliably making larger a quantity of signal charge that can be fetched therefrom and reliably enhancing the fetch efficiency and the image signal-to-noise (S/N) ratio.

In addition, if the ratio of the product of the width and transmission factor of the main line electrode per pixel and the product of the width and transmission factor of the secondary line electrode per pixel is set so that it satisfies the aforementioned condition equation (2), even in the case where a plurality of main line electrodes and a plurality of secondary line electrodes are allocated to 1 pixel, a quantity of signal charge that can be fetched from the detector can be reliably made larger, even if there are fluctuations in the widths and transmission factors of the main and secondary line electrodes.

BRIEF DESCRIPTION OF THE DRAWINGS

The above and other objects and advantages will become apparent from the following detailed description when read in conjunction with the accompanying drawings wherein:

FIG. 5 is a diagram showing an example of combinations of the electrode width and the transmission factor for satisfying the aforementioned condition equation (1) or (2);

DESCRIPTION OF THE PREFERRED EMBODIMENTS

Figure 1A:
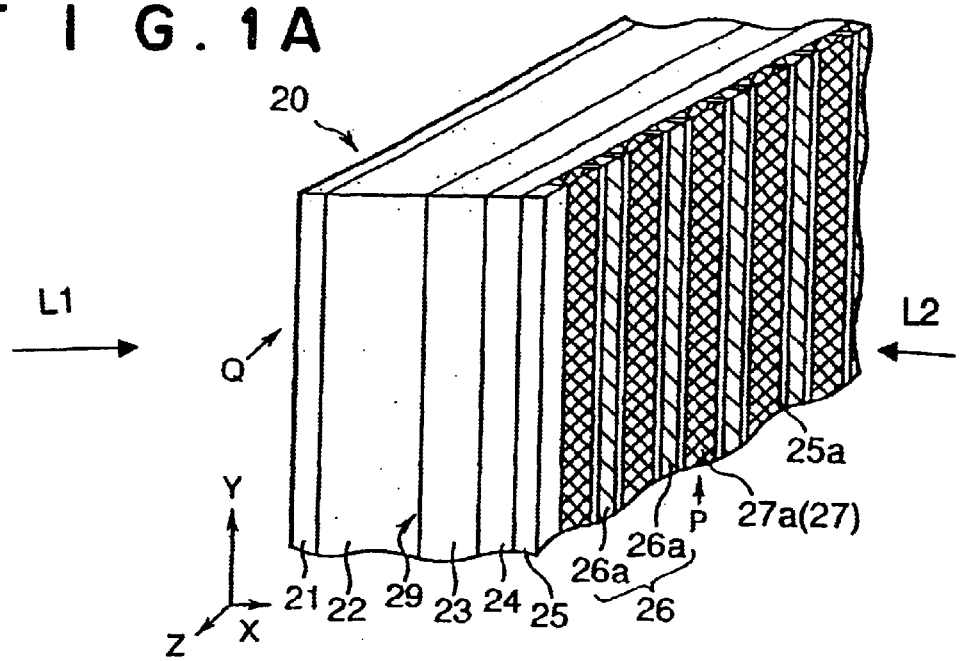
FIG. 1A is a perspective view showing a solid state radiation detector constructed according to a first embodiment of the present invention.
Figure 1B:
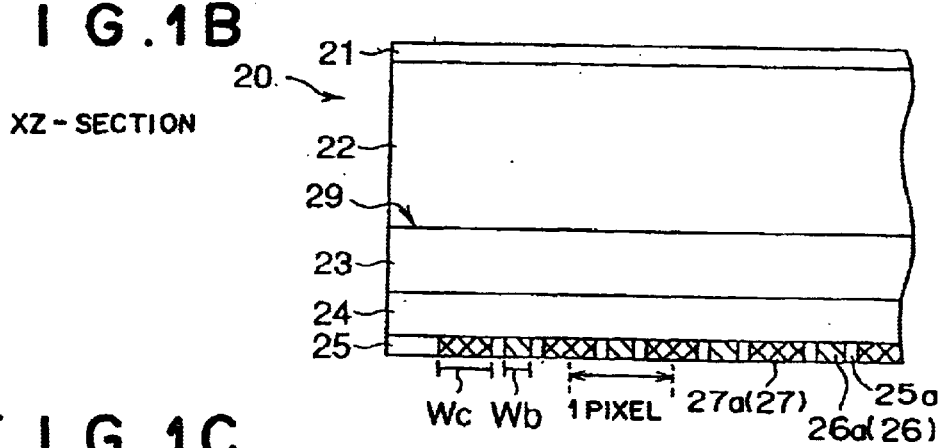
FIG. 1B is an XZ-section of the solid state radiation detector taken in a direction of arrow Q.
Figure 1C:
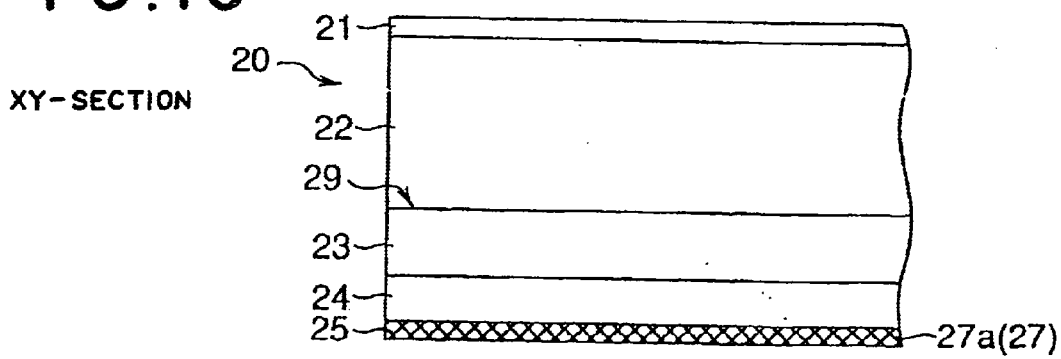
FIG. 1C is an XY-section of the solid state radiation detector taken in a direction of arrow P.

Referring now in greater detail to the drawings and initially to FIG. 1, there is shown a first embodiment of a solid state radiation detector in accordance with the present invention. The solid state radiation detector 20 is constructed of a first electrode layer 21 which has permeability with respect to recording radiation (e.g., X-rays, which will hereinafter be referred to as recording light) L1, a recording photoconductive layer 22 which exhibits electric conduction when irradiated with the recording light L1 transmitted through the first electrode layer 21, a charge transfer layer 23 which operates as substantially an insulator with respect to latent image charge (e.g., negative charge) and also operates as substantially an electric conductor with respect to a transfer charge of the opposite polarity from the latent image charge (in the above example, positive charge), a reading photoconductive layer 24 which exhibits electric conduction when irradiated with reading light (electromagnetic waves for reading) L2, and a second electrode layer 25 which has permeability with respect to the reading light L2, which are stacked in the recited order.

The proper substance of the recording photoconductive layer 22 is a photoconductive substance that has at least one among (1) α-Se (amorphous selenium), (2) plumbic oxide (II) or lead iodide (II), such as PbO, $PbI_2$, etc., and (3) $Bi_{12}(Ge, Si)O_{20}$, $Bi_2I_3$/organic polymer nanocomposite, as its main ingredient.

The substance of the charge transfer layer 23 is more desirable, for example, if the difference between the mobility of negative charge on the first electrode layer 21 and the mobility of positive charge having the opposite polarity is greater (e.g., $10^2$ or greater, preferably $10^3$ or greater). The proper substance is an organic compound (such as a poly N-vinyl carbazole (PVK), N,N'-diphenyl-N,N'-bis(3-methyl phenyl)-(1,1'-biphenyl)-4,4'-diamine (TPD), adiscotic liquid crystal, etc.), a polymer (polycarbonate, polystyrene, PUK) dispersed component of the TPD, and a semiconductor substance such as a Cl-doped α-Se (10 to 200 ppm). Particularly, organic compounds (PVK, TPD, discotic liquid crystal, etc.) are preferred because they have non-photosensitivity. In addition, since the dielectric constant is generally small, the capacities of the charge transfer layer 23 and the reading photoconductive layer 24 become smaller and therefore the signal-fetching efficiency during reading can be made greater. Note that the words "have non-photosensitivity" mean that a substance having non-photosensitivity exhibits almost no electric conduction even when irradiated with the recording light L1 or reading light L2.

The desired substance of the reading photoconductive layer 24 is a photoconductive substance that has at least one among α-Se, Se—Te, Se—As—Te, non-metal phthalocyanine, magnesium phthalocyanine (MgPc), phase II of Vanadyl phthalocyanine (VoPc), and copper phthalocyanine (CuPc), as its main ingredient.

It is preferable that the thickness of the recording photoconductive layer 22 be 50 through 1000 μm in order to sufficiently absorb the recording light L1. In the first embodiment, it is about 500 μm. It is also preferable that the sum total of the thickness of the charge transfer layer 23 and the thickness of the photoconductive layer 24 be ½ or less of that of the recording photoconductive layer 22. In addition, since the responsivity during reading is enhanced if the total thickness becomes thinner and thinner, it is preferable that the thickness be, for example, ¹⁄₁₀ or less, and furthermore, ¹⁄₂₀ or less.

The proper substance of the first electrode layer 21 is, for example, a NESA glass in which a conductive substance is coated on a transparent glass plate.

The light irradiating electrode of the second electrode layer 25 is formed as a stripe electrode 26 in which a large number of elements (main line electrodes for light irradiation) 26a are arrayed in stripe form.

The material and thickness of each element 26a of the stripe electrode 26 can employ indium tin oxide (ITO) with a thickness of 100 nm, Idemitsu indium X-metal oxide (IDIXO, produced by Idemitsu Kosan) with a thickness of 100 nm, aluminum with a thickness of 10 nm, molybdenum with a thickness of 10 nm, etc. By using these, any of them can make the transmission factor $P_b$ with respect to the reading light L2 50% or greater.

Within the second electrode layer 25, there is provided a secondary electrode (charge fetching electrode) 27, which is a conductive member for outputting an electrical signal having a level proportional to the quantity of the latent image charge stored in the charge storage portion 29 formed in the interface between the recording photoconductive layer 22 and the charge transfer layer 23. This secondary electrode 27 is constructed of a great number of elements (secondary line electrodes for fetching electric charge) 27a arrayed in stripe form. The stripe electrode 26 and the secondary electrode 27 are arrayed so that the elements (main line electrodes) 26a and the elements (secondary line electrodes) 27a are alternately disposed in parallel to one another.

The material and thickness of each element 27a of the secondary electrode 27 can employ aluminum of 100 nm in thickness, molybdenum of 100 nm in thickness, chrome of 100 nm in thickness, etc. By using these, any of them can make the transmission factor $P_b$ with respect to the reading light L2 10% or less and prevent a pair of electric charges, which fetch signal charge from the detector, from occurring within the reading photoconductive layer 24 corresponding to the elements 27a.

In addition, each element 26a and each element 27a are spaced a predetermined distance so that they are electrically insulated. The space 25a between both elements is filled with a non-conductive high polymer material, such as polyethylene dispersing a slight amount of pigment (e.g., carbon black), and therefore intercepts the reading light L2.

In this detector 20, the width $W_c$ of the element 27a is made wider than the width $W_b$ of the element 26a, and the transmission factor $P_b$ of the element 26a with respect to the reading light L2 and the transmission factor $P_c$ of the element 27a with respect to the reading light L2 are set so that they satisfy a condition equation of $(W_b \times P_b)/(W_c \times P_c) \geq 1$ (the above-mentioned condition equation (1)).

In this case, in accordance with making the width $W_c$ of the element 27a wider than the width $W_b$ of the element 26a, the stripe electrode 26 and the secondary electrode 27 are electrically connected during recording of an electrostatic latent image so that the secondary electrode 27 can be positively utilized in forming an electric field distribution.

If recording is performed with the stripe electrode 26 and the secondary electrode 27 thus connected, the latent image charge is stored not only at the positions corresponding to the elements 26a but also at the positions corresponding to the elements 27a. Therefore, if the reading light L2 is irradiated to the reading photoconductive layer 24 through the elements 26a during reading, the latent image charge over two elements 27a on both sides of the element 26a is read out through the two elements 27a. In this case, the position corresponding to the element 26a corresponds to the center of a pixel, and the element 26a and the halves of the elements 27a on both sides of the element 26a constitute 1 pixel in the direction where the elements 26a, 27a are arranged.

In this detector 20, capacitor $C_{*a}$ is formed between the first electrode layer 21 and the charge storage portion 29, with the recording photoconductive layer 22 therebetween.

And a quantity of signal charge that can be fetched from the detector 20 becomes the same as the sum total $(Q_a + Q_c)$ of the quantities $(Q_a, Q_c)$ of positive charge distributed to the capacitors $C_{*a}$ and $C_{*c}$, and the positive charge distributed to the capacitor $C_{*b}$ cannot be fetched as signal charge (for the details, see the aforementioned Japanese Patent Application No. 11 (1999)-87922).

For the capacitances of the capacitors $C_{*b}$ and $C_{*c}$ that are determined by the stripe electrode 26 and the secondary electrode 27, the capacitance ratio $(C_b : C_c)$ becomes the width ratio $(W_b : W_c)$ of the elements 26a and 27a. On the other hand, for the capacitance $C_a$ of the capacitor $C_{*a}$ and the capacitance $C_b$ of the capacitor $C_{*b}$, practically a great influence does not appear even if the secondary electrode 27 is provided.

As a result, the quantity of positive charge $(Q_b)$ that is distributed to the capacitor $C_b$ at the time of charge rearrangement during reading can be made smaller than the case where the secondary electrode 27 is not provided, and by that amount, the quantity of signal charge that can be fetched from the detector 20 through the secondary electrode 27 can be made larger than the case where the secondary electrode 27 is not provided.

In addition, since the width $W_b$ of the element 26a, the transmission factor $P_b$ of the element 26a with respect to the reading light L2, the width $W_c$ of the element 27a, and the transmission factor $P_c$ of the element 27a with respect to the reading light L2 are determined so that they satisfy the condition equation (1), the quantity of signal charge that can be fetched from the detector can be made larger with reliability and it becomes possible to enhance the fetch efficiency and the image S/N ratio reliably.

Note that in order to fetch a larger amount of signal charge from the detector, making the width $W_c$ of the element 27a as large as possible and larger than the width $W_b$ of the element 26a is preferred because the capacitance ratio of the capacitors $C_{*b}$, $C_{*c}$, is determined by the width ratio of the elements 26a, 27a. In making the width of the element 27a larger than that of the element 26a, the transmission factors $P_b$, $P_c$ of the elements 26a, 27b with respect to the reading light L2 are set so that they satisfy the above-mentioned condition equation (1).

Furthermore, when eliminating the electric charge remaining within the detector 20, it is preferable that the secondary electrode 27 also have permeability with respect to the reading light L2. Even in this case, by satisfying the above-mentioned condition equation (1), the remaining electric charge can be eliminated without reducing the fetch efficiency and the image S/N ratio.

Figure 2A:
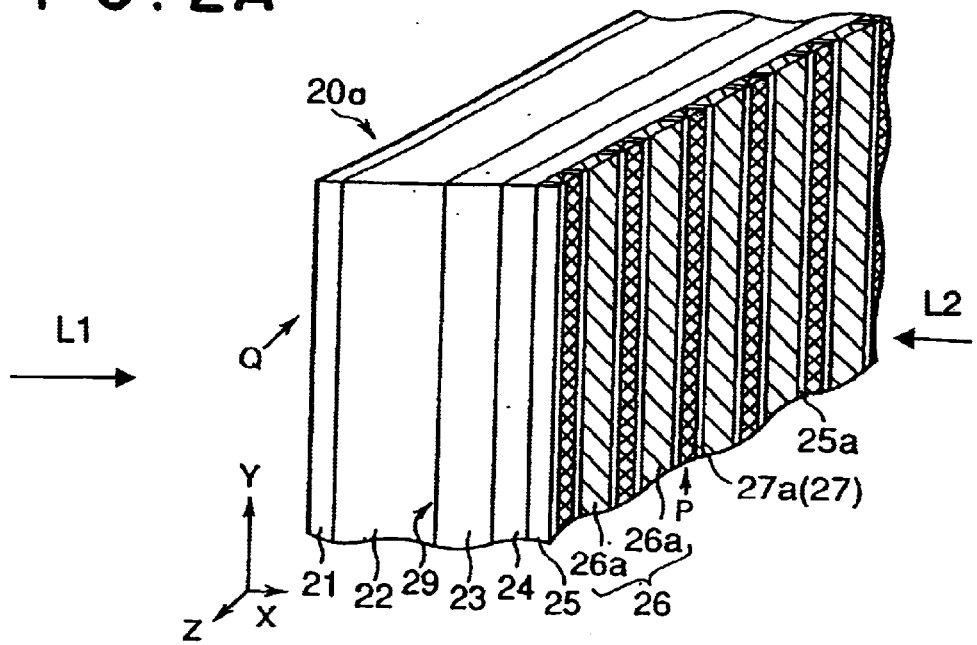
FIG. 2A is a perspective view showing a solid state radiation detector constructed according to a second embodiment of the present invention.
Figure 2B:
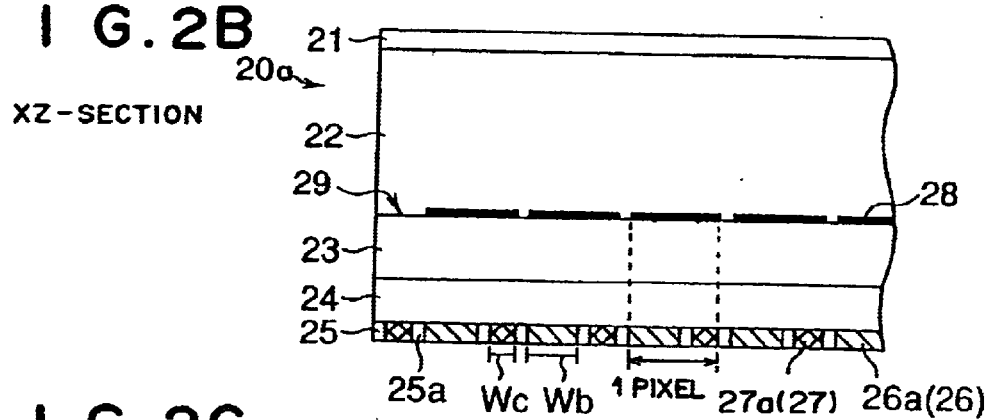
FIG. 2B is an XZ-section of the solid state radiation detector of FIG. 2A taken in a direction of arrow Q.
Figure 2C:
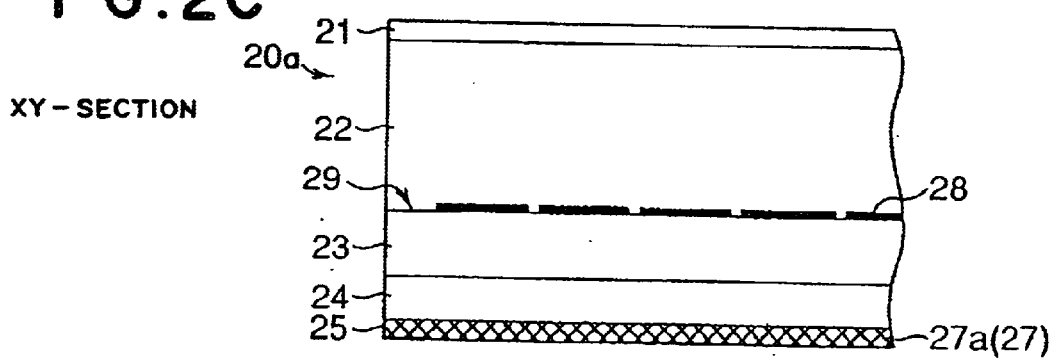
FIG. 2C is an XY-section of the solid state radiation detector of FIG. 2A taken in a direction of arrow P.

FIG. 2 illustrates a solid state radiation detector constructed according to a second embodiment of the present invention. Since the same reference numerals are applied to the same elements as those of the detector 20 of the first embodiment shown in FIG. 1, a description thereof is omitted unless particularly necessary.

The solid state radiation detector 20a of the second embodiment comprises a first electrode layer 21, a recording photoconductive layer 22, a charge transfer layer 23, a reading photoconductive layer 24, and a second electrode layer 25, which are stacked in the recited order. As with the detector 20 of the above-mentioned first embodiment, the light-irradiating electrode of the second electrode layer 25 is constructed of a stripe electrode 26 which consists of a large number of elements 26a, and a great number of elements 27a forming a secondary electrode 27 are provided so that the elements 26a and 27a are alternately arranged in parallel to one another. Each layer is identical with that of the detector 20 of the first embodiment.

In a charge storage portion 29 of the detector 20a of the second embodiment, which is an interface between the recording photoconductive layer 23 and the charge transfer layer 23, a large number of separate, square microplates (micro conductive members) are disposed with spaces so that each microplate is located right above two adjacent elements 26a, 27a. The length of each side of this microplate 28 is set to essentially the same as the pitch, or distance between the centers of two adjacent elements 26a, that is, to essentially the same dimension as the smallest pixel pitch at which resolution can be obtained. The position at which the microplate 28 is arranged corresponds to the position of a pixel on the detector 20a.

In the detector 20a of the second embodiment, the width $W_b$ of the element 26a is made wider than the width $W_c$ of the element 27a, and control voltage is applied so that the voltage across the secondary electrode 27 becomes the same as that across the stripe electrode. With this, it is preferable that a uniform electric field distribution be formed between the first electrode layer 21 and the second electrode layer 25.

In this manner, in the process of recording an electrostatic latent image, the negative charge produced within the recording photoconductive layer 23 can be stored on the microplates 28, and in the reading process, the latent image charge stored on the microplates 28 can freely move on the microplates 28 held at the same potential. Therefore, the latent image charge can be discharged more sufficiently and the amount of the charge left unread can be reduced. Note that the center of the microplate may be disposed right above the center of the element 27a so that the electric charge around a pixel can be collected more easily.

While, in the detector 20a of the second embodiment, the width $W_b$ of the element 26a is made wider than the width $W_c$ of the element 27a, the amount of signal charge that can be fetched from the detector can be made larger with reliability and the fetch efficiency and the image S/N ratio can be reliably enhanced, as with the detector 20 of the first embodiment, if the transmission factor $P_b$ of the element 26a with respect to the reading light L2 and the transmission factor $P_c$ of the element 27a with respect to the reading light L2 are set so that they satisfy the aforementioned condition equation (1).

Figure 3A:
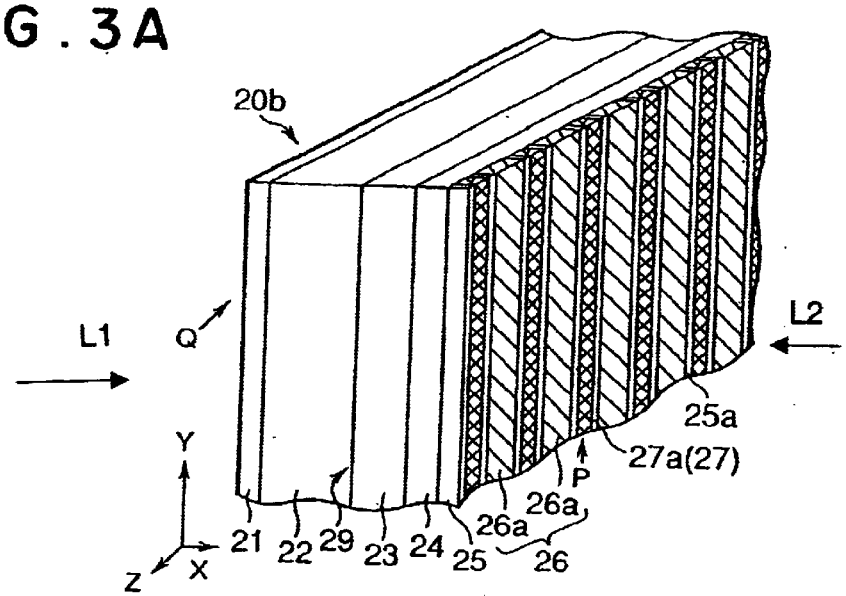
FIG. 3A is a perspective view showing a solid state radiation detector constructed according to a third embodiment of the present invention.
Figure 3B:
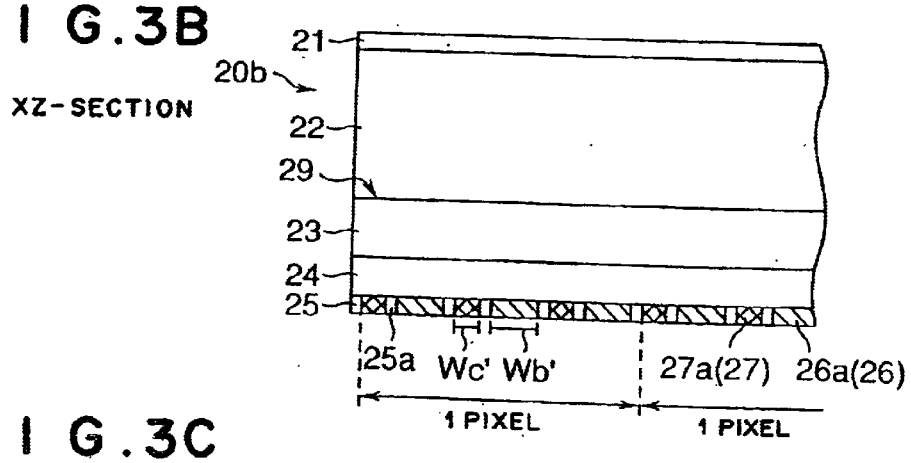
FIG. 3B is an XZ-section of the solid state radiation detector of FIG. 3A taken in a direction of arrow Q.
Figure 3C:
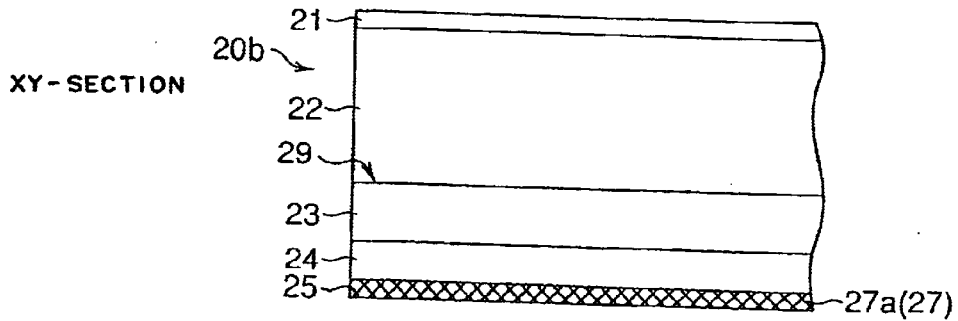
FIG. 3C is an XY-section of the solid state radiation detector of FIG. 3A taken in a direction of arrow P.

FIG. 3 illustrates a solid state radiation detector constructed according to a third embodiment of the present invention. In the figure, the same reference numerals are applied to the same elements as those of the detector 20 of the first embodiment shown in FIG. 1 and therefore a description thereof is omitted unless particularly necessary.

The detector 20b of the third embodiment is constructed such that the microplates 28 of the detector 20a in the second embodiment are removed and that the elements 26a of a stripe electrode 26 and the elements 27b of a secondary electrode 27 are alternately arranged within 1 pixel. In the detector 20b shown in FIG. 3, three elements 26a and three elements 27a are provided within 1 pixel. The transmission factors of the elements 26a constituting 1 pixel are all made the same (transmission factor $P_b$). Similarly, the transmission factors of the elements 27a are all made the same (transmission factor $P_c$).

In the case where recording and reading are performed using the detector 20b, the elements 26a, 27a are handled together in the unit of a pixel. Assuming the size of 1 pixel in the detector 20b of the third embodiment is the same as that of the detector 20a of the above-mentioned second embodiment, the widths $W_b'$, $W_c'$ of the elements 26a, 27a of the detector 20b are set narrower than the widths $W_b$, $W_c$ of the elements 26a, 27a of the detector 20a. However, even in this case, the ratio of the sum total of the widths of the elements 26a per pixel and the sum total of the widths of the elements 27a per pixel becomes the same as the ratio of the width of the element 26a and the width of the element 27a. In addition, the transmission factors of the elements 26a within 1 pixel are the same and the transmission factors of the elements 27a within 1 pixel are assumed to be the same. Therefore, if the transmission factor $P_b$ of the element 26a with respect to the reading light L2 and the transmission factor $P_c$ of the element 27a with respect to the reading light L2 are determined so that they satisfy a condition equation of $(W_b' \times P_b)/(W_c' \times P_c) \geq 5$, the detector 20b of the third embodiment is capable of reliably making larger a quantity of signal charge that can be fetched therefrom and reliably enhancing the fetch efficiency and the image SIN ratio, as with the detectors 20, 20a of the first and second embodiments.

In the case where the transmission factors of the elements 26a within 1 pixel differ from one another and also the transmission factors of the elements 27a within 1 pixel differ from one another, the product of width and transmission factor is calculated for each element 26a and each element 27a within 1 pixel, and the ratio of the sum total of the calculated products for the elements 26a and the sum total of the calculated products for the elements 27a is set so that it satisfies the aforementioned condition equation (2). In this way the aforementioned same advantages are obtainable.

Figure 4A:
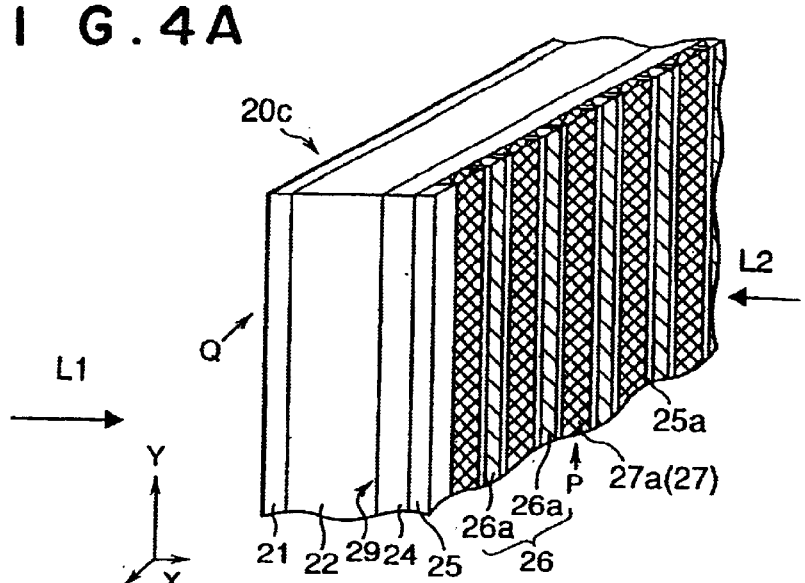
FIG. 4A is a perspective view showing a solid state radiation detector constructed according to a fourth embodiment of the present invention.
Figure 4B:
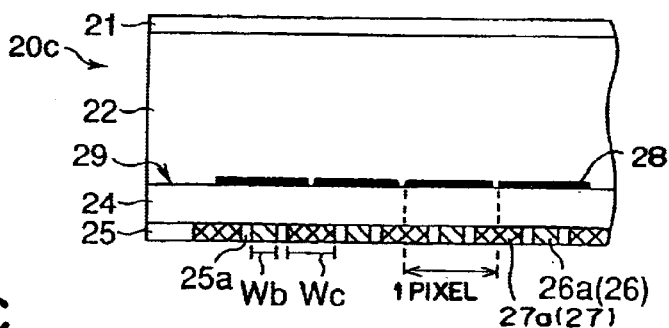
FIG. 4B is an XZ-section of the solid state radiation detector of FIG. 4A taken in a direction of arrow Q.
Figure 4C:
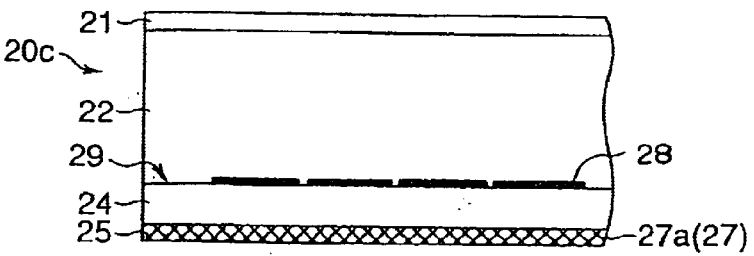
FIG. 4C is an XY-section of the solid state radiation detector of FIG. 4A taken in a direction of arrow P.

FIG. 4 illustrates a solid state radiation detector constructed in accordance with a fourth embodiment of the present invention. In the figure, the same reference numerals are applied to the same elements as those of the detector 20 of the first embodiment shown in FIG. 1, and a description thereof is omitted for avoiding redundancy. The detector 20c in the fourth embodiment is constructed such that the charge transfer layer 23 of the detector 20a in the second embodiment is removed and that the center of a microplate 28 is located right above an element 26a. Since the position of the microplate 28 corresponds to the position of a pixel on the detector 20c, the position corresponding to the element 26a becomes the center of a pixel and therefore the element 26a and the halves of the elements 27a on both sides of the element 26a constitute 1 pixel in the direction where the elements 26a, 27a are arranged.

As with the detector 20a of the aforementioned second embodiment, in the process of recording an electrostatic latent image, the negative charge generated within the recording photoconductive layer 23 can be stored on the microplates 28, and in the reading, process, the latent image charge stored on the microplates 28 can freely move on the microplates 28 held at the same potential at all times. Therefore, the detector 20c of the fourth embodiment is capable of more sufficiently discharging the latent image charge and reducing the amount of the charge left unread.

While in the detector 20c the width $W_c$ of the element 27a is made wider than the width $W_b$ of the element 26a, the quantity of signal charge that can be fetched from the detector 20c can be made larger with reliability and the fetch efficiency and the image S/N ratio can be reliably enhanced, as with the detector 20 of the first embodiment, if the transmission factor $P_b$ of the element 26a with respect to the reading light L2 and the transmission factor $P_c$ of the element 27a with respect to the reading light L2 are set so that they satisfy the aforementioned condition equation (1).

While the present invention has been described with reference to the preferred embodiments thereof, the invention is not to be limited to the details given herein, but may be modified within the scope of the invention hereinafter claimed.

For example, the combination of the electrode width and the transmission factor for satisfying the condition equation (1) is not limited to those of the aforementioned embodiments. FIG. 5 shows an example of combinations of an electrode width and a transmission factor for satisfying the condition equation (1) or (2). Note that an example of combinations that cannot satisfy the condition equation (1) is shown in (e) and (f) of FIG. 5. As shown, while various combinations can be adopted, an enhancement in the reading efficiency becomes greater, as the total light quantity ratio $(W_b \times P_b)/(W_c \times P_c)$, which satisfies the condition equation (2) as well as the condition equation (1), becomes greater.

In addition, although in all the detectors of the aforementioned embodiments the recording photoconductive layer exhibits electric conduction when irradiated with the recording radiation, the recording photoconductive layer of the detector according to the present invention is not always limited to this, but may be one which exhibits electric conduction when irradiated with light emitted by excitation of the recording radiation (see the aforementioned Japanese Patent Application No. 10 (1998)-271374). In this case, a wavelength converting layer, called an x-ray scintillator which converts the recording radiation to light of another wavelength such as blue light, may be stacked on the surface of the first electrode layer. It is desirable that the wavelength converting layer employ for example, cesium iodide (CsI). It is also desirable that the first electrode layer have permeability with respect to light emitted from the wavelength converting layer by excitation of the recording radiation.

In the detectors 20, 20a, and 20b of the aforementioned embodiments, while the charge transfer layer is provided between the recording photoconductive layer and the reading photoconductive layer and also the charge storage portion is formed in the interface between the recording photoconductive layer and the charge transfer layer, the charge transfer layer may be replaced with a trapping layer. In the case of a trapping layer, latent image charge is trapped in the trapping layer, and is stored within the trapping layer, or in the interface between the trapping layer and the recording photoconductive layer. Also, the microplate may be provided for each pixel in the interface between the trapping layer and the recording photoconductive layer.

Figure 6A:
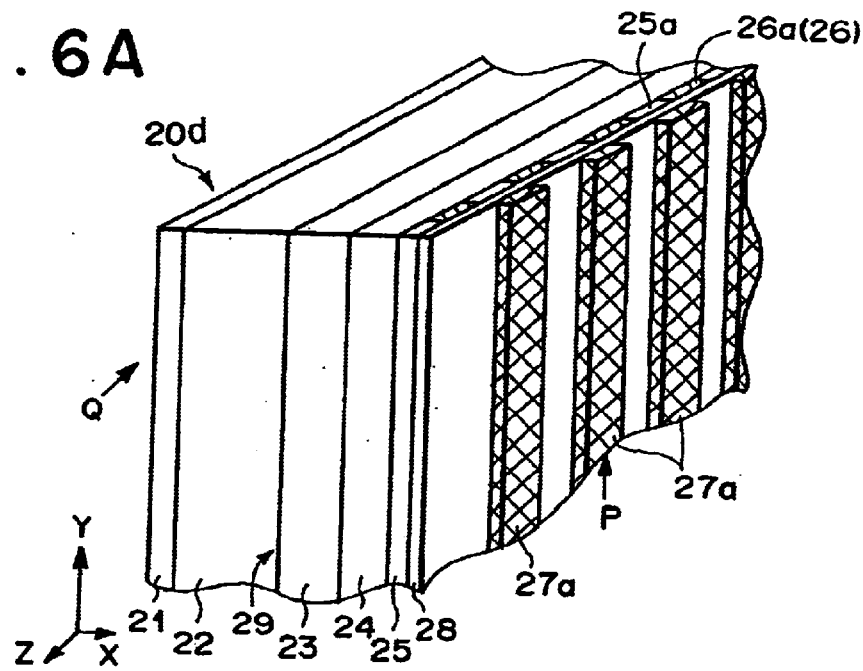
FIG. 6A is a perspective view showing a solid state radiation detector constructed according to a fifth embodiment of the present invention.
Figure 6B:
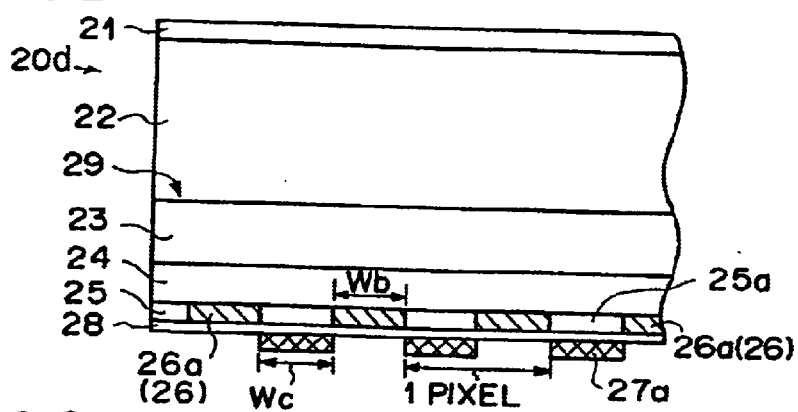
FIG. 6B is an XZ-section of the solid state radiation detector of FIG. 6A taken in a direction of arrow Q.
Figure 6C:
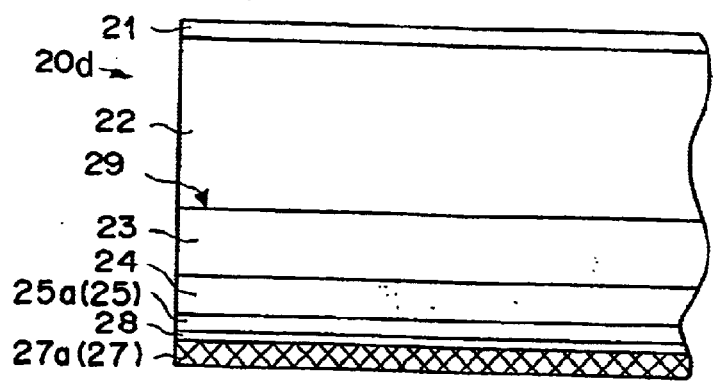
FIG. 6C is an XY-section of the solid state radiation detector of FIG. 6A taken in a direction of arrow P.

Furthermore, as shown in FIG. 6, in a detector 20d (where an insulating layer 28 having permeability with respect to reading light is interposed between the elements 26a of a main line electrode 26 for light irradiation and the elements 27a of a secondary line electrode 27 for fetching electric charge), proposed in Japanese Patent Application No. 11 (1999)-266997, the electrode width and the transmission factor may be set so that they satisfy the above-mentioned condition equation (1) or (2).

In addition, all of the contents of the Japanese Patent Application Nos. 11(1999)-207283 and 2000-209529 are incorporated into this specification by reference.

What is claimed is:

1. A solid state radiation detector comprising:
    a first electrode layer having permeability with respect to recording radiation, or light emitted by excitation of said radiation;
    a recording photoconductive layer which exhibits electric conduction when irradiated with said recording radiation or said light;
    a reading photoconductive layer which exhibits electric conduction when irradiated with reading light; and
    a second electrode layer comprising a plurality of main line electrodes and a plurality of secondary line electrodes, wherein said main and secondary line electrodes are alternately arranged in parallel to one another;
    said first electrode layer, said recording photoconductive layer, said reading photoconductive layer, and said second electrode layer being stacked in the recited order;
    said main line electrodes having permeability with respect to said reading light, said secondary line electrodes outputting an electrical signal which has a level proportional to a quantity of latent image charge stored in a charge storage portion formed between said recording photoconductive layer and said reading photoconductive layer;
    wherein a width $W_b$ of each of said main line electrodes, a transmission factor $P_b$ of each of said main line electrodes with respect to said reading light, a width $W_c$ of each of said secondary line electrodes, and transmission factor $P_c$ of each of said secondary line electrodes with respect to said reading light satisfy a condition equation of $(W_b \times P_b)/(W_c \times P_c) \geq 1$, and said transmission factor $P_b$ and said transmission factor $P_c$ are different values.

2. The solid state radiation detector as set forth in claim 1, wherein the width $W_b$ of said main line electrode, the transmission factor $P_b$ of said main line electrode with respect to said reading light, the width $W_c$ of said secondary line electrode, and the transmission factor $P_c$ of said secondary line electrode with respect to said reading light satisfy a condition equation of $(W_b \times P_b)/(W_c \times P_c) \geq 5$.

3. The solid state radiation detector as set forth in claim 1, wherein the material of said main line electrode is any one among indium tin oxide (ITO), Idemitsu indium X-metal oxide (IDIXO, produced by Idemitsu Kosan), aluminum, and molybdenum.

4. The solid state radiation detector as set forth in claim 2, wherein the material of said main line electrode is any one among indium tin oxide (ITO), Idemitsu indium X-metal oxide (IDIXO, produced by Idemitsu Kosan), aluminum, and molybdenum.

5. The solid state radiation detector as set forth in claim 1, wherein the material of said secondary line electrode is any one among aluminum, molybdenum, and chrome.

6. The solid state radiation detector as set forth in claim 2, wherein the material of said secondary line electrode is any one among aluminum, molybdenum, and chrome.

7. The solid state radiation detector as set forth in claim 3, wherein the material of said secondary line electrode is any one among aluminum, molybdenum, and chrome.

8. The solid state radiation detector as set forth in claim 1, wherein said width $W_b$ of each of said main line electrodes is different than said width $W_c$ of each of said secondary line electrodes.

9. The solid state radiation detector as set forth in claim 8, wherein said width $W_b$ of each of said main line electrodes is less than said width $W_c$ of each of said secondary line electrodes.

10. The solid state radiation detector as set forth in claim 8, wherein said width $W_b$ of each of said main line electrodes is greater than said width $W_c$ of each of said secondary line electrodes.

* * * * *